US005504074A

United States Patent [19]
D'Amato et al.

[11] Patent Number: 5,504,074
[45] Date of Patent: Apr. 2, 1996

[54] ESTROGENIC COMPOUNDS AS ANTI-ANGIOGENIC AGENTS

[75] Inventors: Robert J. D'Amato, Lancaster, Pa.; Moses J. Folkman, Brookline, Mass.

[73] Assignee: Children's Medical Center Corporation, Boston, Mass.

[21] Appl. No.: 102,767

[22] Filed: Aug. 6, 1993

[51] Int. Cl.$^6$ .................................................. A61K 31/56
[52] U.S. Cl. ..................... 514/182; 514/178; 514/179; 514/180; 514/177
[58] Field of Search ..................... 514/182, 178

[56] References Cited

U.S. PATENT DOCUMENTS

| | | | |
|---|---|---|---|
| 4,172,132 | 10/1979 | Draper et al. | 514/182 |
| 4,522,758 | 6/1985 | Ward et al. | |
| 4,743,597 | 5/1988 | Javitt et al. | 514/182 |
| 5,001,116 | 3/1991 | Folkman et al. | |

FOREIGN PATENT DOCUMENTS

WO93/03729  3/1993  WIPO.

OTHER PUBLICATIONS

Wheeler et al., Mutation Research vol. 171, pp. 31–41, 1986. Chemical Abstract No. 54822z, "Mitotic inhibition and aneuploidy induction by naturally occurring and synthetic estrogens in Chinese hamster cells in vitro," vol. 105, No. 7, Aug. 18, 1986.
Boyé et al., Helvetica Chimica Acta 72:1690–1696, 1989, "185. Deaminocolchinyl Methyl Ether: Synthesis from 2,3,4,4'-Tetramethoxybiphenyl-2-carbaldehyde. Comparison of Antitubulin . . . Analogs."Crum et al., Science 230:1375–1378, 1985, "A New Class of Steroids Inhibits Angiogenesis in the Presence of Heparin or a Heparin Fragment."Fitzgerald, Biochem. Pharmacol. 25:1383–1387, 1976, "Molecular Features of Colchicine Associated with Antimitotic Activity and Inhibition of Tubulin Polymerization."Getahun et al., J. Med. Chem. 35:1058–1067, 1992, "Synthesis of Alkoxy–Substituted Diaryl Compounds and Correlation of Ring Separation with Inhibition of Tubulin Polymerization: . . . Conditions."Hartley-Asp et al., Mutation Research 143:231–235, 1985, "Diethylstilbestrol induces metaphase arrest and inhibits microtubule assembly."Huber et al., Bioorg. Med. Chem. Lett. 1:243–246, 1991, "Tubulin Binding of Conformationally Restricted Bis–Aryl Compounds."Lin et al., Molecular Pharmacology 34:200–208, 1988, "Interactions of Tubulin with Potent Natural and Synthetic Analogs of the Antimitotic Agent Combretastatin: a Structure–Activity Study."Lincoln et al., Biochemistry 30: 1179–1187, 1991, "Conformation of Thiocolchicine and Two B–Ring–Modified Analogues Bound to Tubulin Studied with optical Spectroscopy."Lottering et al., Cancer Research 52:5926–5932, 1992, "Effects of 17β–Extradiol Metabolites on Cell Cycle Events in MCF–7 Cells."Nakamura et al., Chem. Pharm. Bull. 10:281–290, 1962, "Studies on the Total Synthesis of dl–Colchiceine. I. Synthesis of 3–Hydroxy–9,10,11–trimethoxy–1,2,3,4,6,7–hexahydro–5H–dibenzo[a,c]cycloheptatrien–5–one."Paull et al., Cancer Research 52:3892–3900, 1992, "Identification of Novel Antimitotic Agents Acting at the Tubulin Level by Computer–assisted Evaluation of Differential Cytotoxicity Data."Rao et al., Experimental Cell Research 48:71–81, 1967, "Structural Specificity of Estrogens in the Induction of Mitotic Chromatid Non–Disjunction in HeLa Cells."Ravindra, J. Indian Inst. Sci. 64:27–35, 1983, "Effect of estradiol on the in vitro assembly of rat brain tubulin."Sakakibara et al., Mutation Research 263:269–276, 1991, "Effects of diethylstilbestrol and its methyl ethers on aneuploidy induction and microtubule distribution in Chinese hamster V79 cells."Sato et al., Chem. Pharm. Bull. 40:182–184, 1992, "Effect of Estradiol and Ethynylestradiol on Microtubule Distribution in Chinese Hamster V79 Cells."Sato et al., Gann 75:1046–1048, 1984, "Disruptive Effect of Diethylstilbestrol on Microtubules."Sawada et al., Mutation Research 57:175–182, 1978, "Colchicine–Like Effect of Diethylstilbestrol (DES) On Mammalian Cells In Vitro."Seegers et al., J. steroid Biochem. 32:797–809, 1989, "The Cytotoxic Effects of Estradiol–17β, Catechol–estradiols and Methoxyestradiols on Dividing MCF-7 and HeLa Cells."Sharp et al., Carcinogenes is 6:865–871, 1985, "Diethylstilboestrol: the binding and effects of diethylstilboestrol upon the polymerisation and depolymerisation of purified microtubule protein in vitro."Spicer et al., Molecular and Cellular Endocrinology 64:119–126, 1989, "Catecholestrogens inhibit proliferation and DNA synthesis of porcine granulosa cells in vitro: . . . catecholamines."Sternlicht et al., The Journal of Biological Chemistry 254:10540–10550, 1979, "Colchicine Inhibition of Microtubule Assembly via Copolymer Formation."Seegers et al., Meeting Abstract of Joint NCI–Ist Symp. Third Ist Int'l Symp. Biology and Therapy of Breast Cancer. Sep. 25–27, 1989, Genoa, Italy, A58, 1989, "Cyclic–Amp and Cyclic–GMP Production . . . Cells."Sun et al., J. Med. Chem. 36:544–551, 1993, "Antitumor Agnets. 139. Synthesis and Biological Evaluation of Thiocolchicine Analogs 5,6–Dihydro–6(S)–(acyloxy)–and 5,6–Dihydro–6(S)–[(acroyloxy)methyl]–1,2,3 . . . ".
Sunagawa et al., Chem. Pharm. Bull. 9:81–83, 1961, "Synthesis of Colchicine; Syntehsis of dl–Demethyoxydeoxy–hexahydrocolchicine."Tsutsui et al., Toxic. in Vitro 4:75–84, 1990, "Comparison of Human Versus Syrian Hamster Cells in Culture for Induction of Mitotic Inhibition, Binucleation and Multinucleation, Following Treatment with Four . . . ".
van Tamelen et al., Tetrahedron 14:8–34, 1961, "The Synthesis of Colchicine."Wheeler et al., Cytoskel. 7:235–247, 1987, "Mitotic Inhibition and Chromosome Displacement Induced by Estradiol in Chinese Hamster Cells."Oppolzer et al., Helvetica Chimica Acta 63:1703–1707, 1980, "177. The Enantioselective Synthesis of (+)–Estradiol from 1,3–Dihydrobenzo[c]thiophene–2,2–dioxide by Sucessive Thermal S02–Extrusion . . . Reactions."Research Plus Catalogue, pp. 50–58, 1993.

(List continued on next page.)

*Primary Examiner*—Rebecca Cook
*Attorney, Agent, or Firm*—Fish & Richardson

[57] ABSTRACT

The application discloses methods of treating mammalian diseases characterized by undesirable angiogenesis by administering estradiol derivatives including those comprising colchicine or combretastatin A-4 structural motifs of the general formulae found below in a dosage sufficient to inhibit cell mitosis. The application discloses novel compounds used in the methods.

7 Claims, 3 Drawing Sheets

OTHER PUBLICATIONS

Gross et al., Proc. Natl. Acad. Sci. USA 78:1176–1180, 1981, "Inhibition of tumor growth, vascularization, and collagenolysis in the rabbit cornea by medroxyprogesterone."Poli et al., Proc. Natl. Acad. Sci. USA 87:782–785, 1990, "Tumor necrosis factor α functions in an autocrine manner in the unduction of human immunodeficiency virus expression."Evans et al., J. Am. Chem. Society 103:5813–5821, 1981, "A Convergent Total Sythesis of (+)–Colchicine and (+)–Desacetamidoisocolchicine."CA104:142406, Ochs et al, Cancer Res., 46(3) 1224–32, 1986.

CA86:452863, Yasuda et al, Anat. Embroyol, 174(3), 1986, 289–300.

BA93:119738, Mayol et al, Carcinogenesis, 13(12) 1992, 2381–2388.

ESTROGENIC COMPOUNDS AS ANTI-ANGIOGENIC AGENTS

BACKGROUND OF THE INVENTION

This invention relates to treating disease states characterized by abnormal cell mitosis.

Cell mitosis is a multi-step process that includes cell division and replication (Alberts, B. et al. In The *Cell*, pp. 652–661 (1989); Stryer, E. *Biochemistry* (1988)). Mitosis is characterized by the intracellular movement and segregation of organelles, including mitotic spindles and chromosomes. Organelle movement and segregation are facilitated by the polymerization of the cell protein tubulin. Microtubules are formed from α and β tubulin polymerization and the hydrolysis of guanosine triphosphate (GTP). Microtubule formation is important for cell mitosis, cell locomotion, and the movement of highly specialized cell structures such as cilia and flagella.

Microtubules are extremely labile structures that are sensitive to a variety of chemically unrelated antimitotic drugs. For example, colchicine and nocadazole are anti-mitotic drugs that bind tubulin and inhibit tubulin polymerization (Stryer, E. *Biochemistry* (1988)). When used alone or in combination with other therapeutic drugs, colchicine may be used to treat cancer (WO-9303729-A, published Mar. 4, 1993; J03240726-A, published Oct. 28, 1991), alter neuromuscular function, change blood pressure, increase sensitivity to compounds affecting sympathetic neuron function, depress respiration, and relieve gout (*Physician's Desk Reference*, Vol. 47, p. 1487, (1993)).

Estradiol and estradiol metabolites such as 2methoxyestradiol have been reported to inhibit cell division (Seegers, J. C. et al. *J. Steroid Biochem.* 32, 797–809 (1989); Lottering, M-L. et al. *Cancer Res.* 52, 5926–5923 (1992); Spicer, L. J. and Hammond, *J. M. Mol. and Cell. Endo.* 64, 119–126 (1989); Rao, P. N. and Engelberg, *J. Exp. Cell Res.* 48, 71–81 (1967)). However, the activity is variable and depends on a number of in vitro conditions. For example, estradiol inhibits cell division and tubulin polymerization in some in vitro settings (Spicer, L. J. and Hammond, J. M. *Mol. and Cell. Endo.* 64, 119–126 (1989); Ravindra, R., *J. Indian Sci.* 64(c) (1983)), but not in others (Lottering, M-L. et al. *Cancer Res.* 52, 5926–5923 (1992); Ravindra, R., *J. Indian Sci.* 64(c) (1983)). Estradiol metabolites such as 2-methoxyestradiol will inhibit cell division in selected in vitro settings depending on whether the cell culture additive phenol red is present and to what extent cells have been exposed to i5 estrogen. (Seegers, J. C. et al. Joint NCI-IST Symposium. Biology and Therapy of Breast Cancer. Sep. 25–Sep. 27, 1989, Genoa, Italy, Abstract A58).

Numerous diseases are characterized by abnormal cell mitosis. For example, uncontrolled cell mitosis is a hallmark of cancer. In addition, cell mitosis is important for the normal development of the embryo, formation of the corpus luteum, wound healing, inflammatory and immune responses, angiogenesis and angiogenesis related diseases.

SUMMARY OF THE INVENTION

I have discovered that certain compounds within the scope of the general formulae set forth below in the claims are useful for treating mammalian diseases characterized by undesired cell mitosis. Without wishing to bind myself to any particular theory, such compounds generally inhibit microtubule formation and tubulin polymerization and/or depolymerization. Compounds within the general formulae having said inhibiting activity are preferred. Preferred compositions may also exhibit a change (increase or decrease) in estrogen receptor binding, improved absorbtion, transport (e.g. through blood-brain barrier and cellular membranes), biological stability, or decreased toxicity. I have also discovered certain compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

Other features and advantages of the invention will be apparent from the following description of preferred embodiments thereof.

COMPOUNDS ACCORDING TO THE INVENTION

As described below, compounds that are useful in accordance with the invention include novel estradiol derivatives that bind tubulin, inhibit microtubule formation or exhibit anti-mitotic properties. Specific compounds according to the invention are described below.

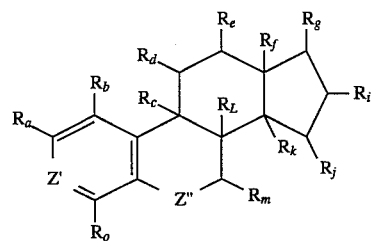

wherein:
I.$R_a$–$R_o$ are defined as follows:
A) each $R_a$, $R_b$, $R_c$, $R_d$, $R_e$, $R_f$, $R_i$, $R_j$, $R_k$, $R_L$, $R_m$, $R_o$, independently is —$R_1$, —$OR_1$, —$OCOR_1$, —$SR_1$, —F, —$NHR_2$, —Br, —I; and $R_g$ is —$R_1$ —$OR_1$, —$OCOR_1$, —$SR_1$, —F, —$NHR_2$, —Br, —I, or —C≡CH; or B) each $R_a, R_b, R_c, R_f, R_k, R_L, R_o$, independently is —$R_1$, —$OR_1$, —$OCOR_1$, —$SR_1$, —F, —$NHR_2$, —Br, or —I; and each $R_d, R_e, R_j, R_m$, independently is =O, —$R_1$, —$OR_1$, —$OCOR_1$, —$SR_1$, —F, $NHR_2$, —Br or —I; and $R_g$ is =O, —$R_1$, —$OR_1$, —$OCOR_1$, —$SR_1$, —F, —$NHR_2$, —BR, —I, or —C≡CH II. Z' is defined as follows:

A) Z' is X, where X is

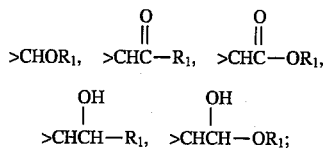

or

B) Z' is

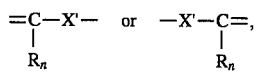

where $R_n$ is —$R_1$, —$OR_1$, —$SR_1$, —F, —$NHR_2$, —BR or —I; and X' is X, as defined above; or X' is >C=O; and III. Z" is defined as follows:

A) Z" is Y, where Y is

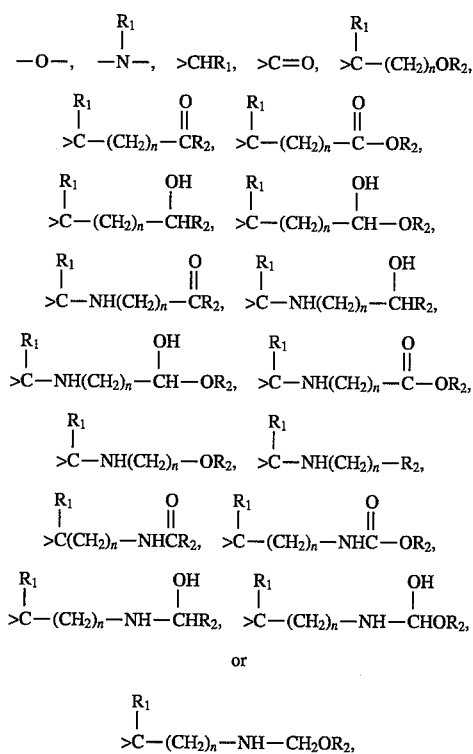

where n is 0–6; or

B) Z" is

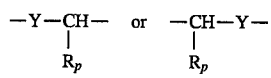

where $R_p$ is —$R_1$, $OR_1$, —$SR_1$, —F, —$NHR_2$, —Br or —I and Y is defined as in III (A); and IV. provided that when each Rb, Rc, Rd, Re, Ri, Rj, Rk, RL, Rm, and Ro is H;
$R_f$ is —$CH_3$;
$R_g$ is —OH;
Z' is >COH; and
Z" is >CH2;
then $R_a$ is not —H;

where, in each formula set forth above, each $R_1$ and $R_2$ independently is —H, or a substituted or unsubstituted alkyl, alkenyl or alkynl group of up to 6 carbons. Those skilled in the art will appreciate that the invention extends to other compounds within the formulae given in the claims below, having the described characteristics. These characteristics can be determined for each test compound using the assays detailed below and elsewhere in the literature.

Figure 3:
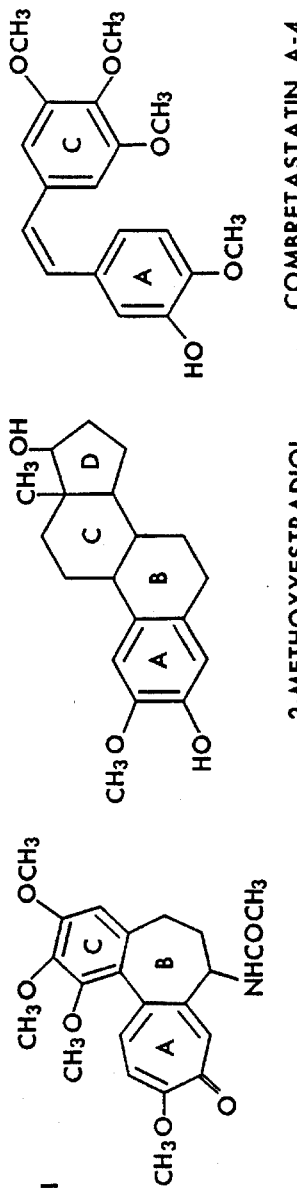
FIG. 3 depicts: I. colchicine, 2-methoxyestradiol and combretastatin A-4, and II. various estradiol derivatives comprising colchicine (a–c) or combretastatin A-4 (d) structural motifs as described below.
Figure 3:
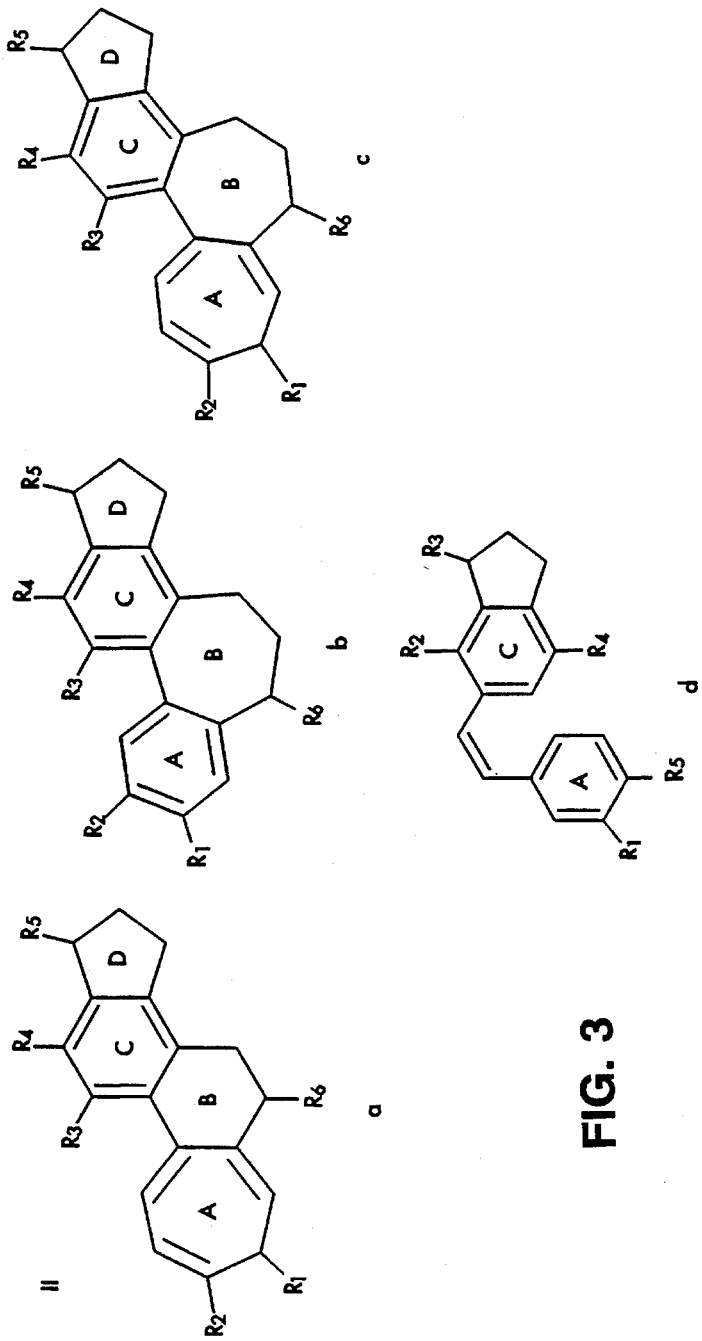

Without wishing to bind myself to specific mechanisms or theory, it appears that certain compounds that are known to inhibit microtubule formation, bind tubulin and exhibit anti-mitotic properties such as colchicine and combretastatin A-4 share certain structural similarities with estradiol. FIG. 3 illustrates the molecular formulae of estradiol, colchicine, combretastatin A-4, and improved estradiol derivatives that bind tubulin, inhibit microtubule assembly and exhibit anti-mitotic properties. Molecular formulae are drawn and oriented to emphasize structural similarities between the ring structures of colchicine, combretastatin A-4, estradiol, and certain estradiol derivatives. Estradiol derivatives are made by incorporating colchicine or combretastatin A-4 structural motifs into the steroidal backbone of estradiol.

FIG. 3, part I, depicts the chemical formulae of colchicine, 2-methoxyestradiol and combretastatin A-4. FIG. 3, part II a–d, illustrates estradiol derivatives that comprise structural motifs found in colchicine or combretastatin A-4. For example, part II a–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 3, may be fully saturated as found in 2-methoxyestradiol. $R_{1-6}$ represent a subset of the substitution groups found in the claims. Each $R_1 \rightarrow R_6$ can independently be defined as —$R_1$, $OR_1$, —$OCOR_1$, —$SR_1$, —F, —$NHR_2$, —Br, —I, or —C≡CH.

DETAILED DESCRIPTION OF THE INVENTION

Anti-mitotic Activity In Situ

Anti-mitotic activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Mitotic Activity In Vitro

Anti-mitotic activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture (all concentrations refer to a final reaction volume of 0.25 μl) contains 1.0M monosodium glutamate (ph 6.6), 1.0mg/ml (10 μM) tubulin, 1.0 mM $MgCl_2$, 4% (v/v) dimethylsulfoxide and 20–75 μM of a composition to be tested. The 0.24 ml react mixtures are incubated for 15 min. at 37° C. and then chilled on ice. After addition of 10 μl 12.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 below.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

Improved Estradiol Derivative Synthesis

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., Ber 109, 2948 (1976); Oppolzer, D. A. and Roberts, D. A. *Helv. Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8–34 (1961); Evans, D. E. et al. JACS 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index*, 11th Ed., Merck & Co., Inc., Rahway, NJ USA (1989), pp. 583–584).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01-1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents conventional in the art having regard to the type of formulation in question, for example, those suitable for oral administration may include flavoring agents.

EXAMPLE 1

Figure 1:
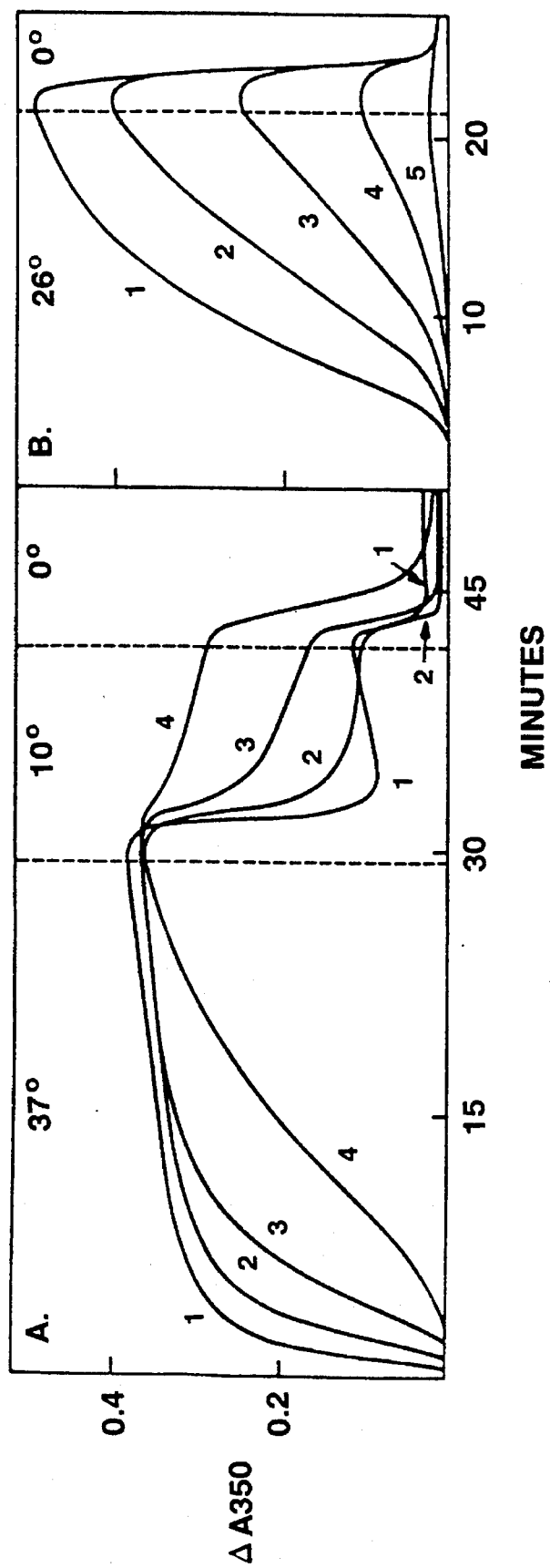
FIG. 1 is a graph illustrating the inhibition of tubulin polymerization by 2-methoxyestradiol described by Example 1 below.

FIG. 1 illustrates the inhibition of tubulin polymerization by 2-methoxyestradiol.

A. Each reaction mixture (all concentrations refer to the final reaction volume of 0.25 ml) contained 1.0 M monosodium glutamate (pH 6.6), 1.0 mg/ml (10 μM) tubulin, 1.0 mM $MGCl_2$, 4% (v/v) dimethylsulfoxide, and either 0 (curve 1), 20 μM (curve 2), 40 μM (curve 3), or 75 μM (curve 4) 2-methoxyestradiol. The 0.24 ml reaction mixtures were incubated for 15 min at 37° C. and chilled on ice. After addition of 10 μl of 2.5 mM GTP the reaction mixtures were transferred to cuvettes held at 0° C., and baselines were established. At time zero the temperature controller was set at 37° C. At the times indicated by the vertical dashed lines the temperature controller was set at the indicated temperatures.

B. Each reaction mixture contained 0.8M monosodium glutamate (pH 6.6), 1.2 mg/ml (12 μM) tubulin, 4% (v/v) dimethylsulfoxide, and either 0 (curve 1), 1.0 μM (curve 2), 2.0 μM (curve 3), 3.0 μM (curve 4), or 4.0 μM (curve 5) 2-methoxyestradiol. The 0.24 ml reaction mixtures were incubated for 15 min at 26° C. and chilled on ice. After addition of 10 μl of 10 mM GTP the reaction mixtures were transferred to cuvettes held at 0° C., and baselines were established. At time zero the temperature controller was set at 26° C. At the time indicated by vertical dashed line the temperature controller was set at 0° C.

EXAMPLE 2

Transmission electron microscopy (TEM) can show differences between the morphology of polymerized tubulin formed in the absence or presence of 2-methoxyestradiol. After a 30 min incubation (37° C.) of reaction mixtures containing the components described in Example 1, 75 μM 2-methoxyestradiol was added, and aliquots were placed on 200-mesh carbon coated copper grids and stained with 0.5% (w/v) uranyl acetate. TEM magnifications from 23,100X to 115,400X were used to visualize differences in tubulin morphology.

EXAMPLE 3

Figure 2:
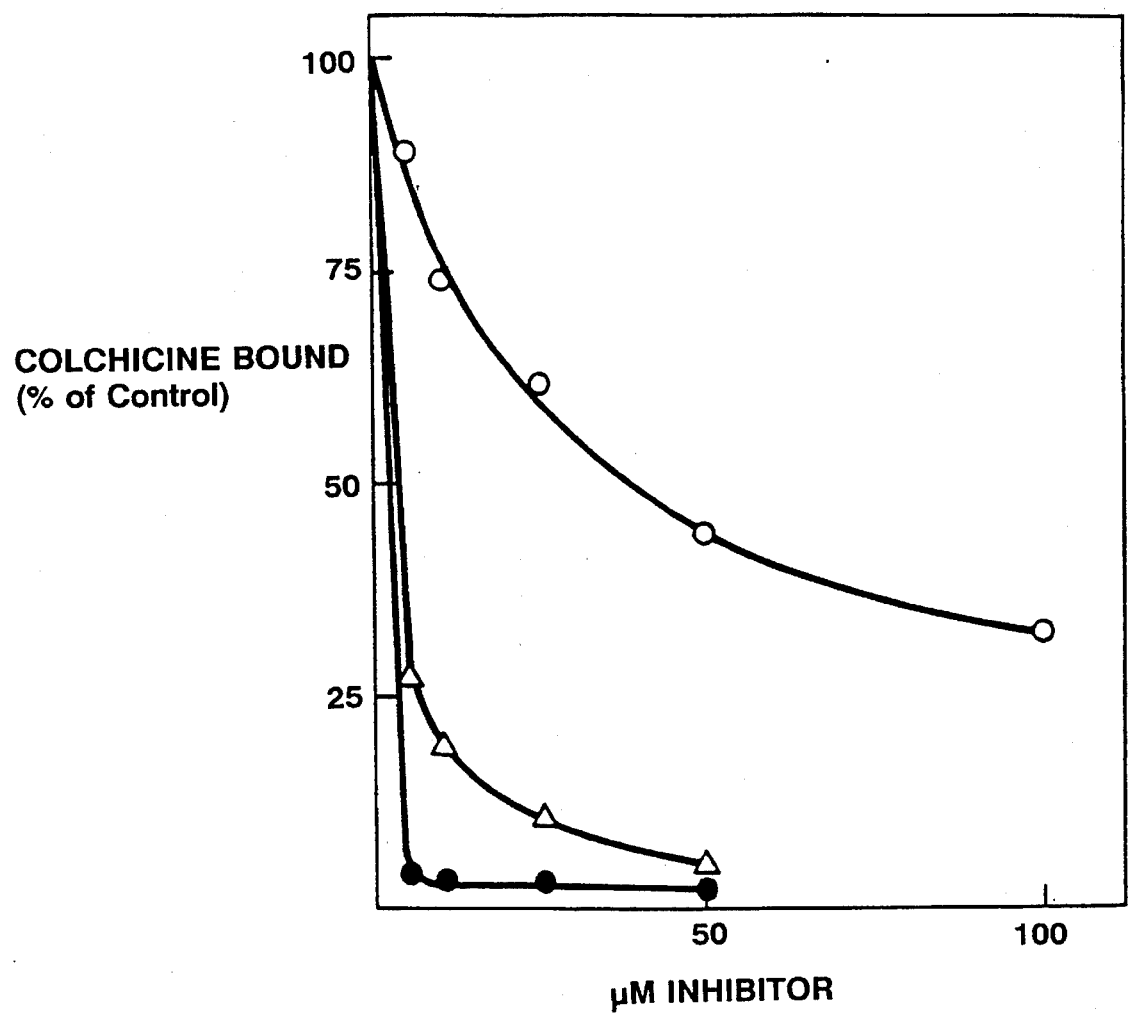
FIG. 2 is a graph illustrating the inhibition of colchicine binding to tubulin by 2-methoxyestradiol described by Example 2 below.

FIG. 2 illustrates that 2-methoxyestradiol inhibits colchicine binding to tubulin. Reaction conditions were as described in the text, with each reaction mixture containing 1.0 μM tubulin, 5% (v/v) dimethyl sulfoxide, 5 μM [$^3$H] colchicine, and inhibitor at the indicated concentrations. Incubation was for 10 min at 37° C. Symbols as follows: ○, 2-methoxyestradiol; ●, combretastatin A-4; ∆, dihydrocombretastatin A-4. Combretastatin A-4 and dihydrocombretastatin A-4 are compounds with anti-mitotic activity similar to colchicine.

EXAMPLE 4

Table 1 illustrates the inhibitory effects on tubulin polymerization in vitro exhibited by estradiol or estradiol derivatives, plant anti-mitotic compounds such as colchicine, combretastatin A-4 or other plant compounds. The method is given in Example 1.

EXAMPLE 5

Table 2 lists estrogens, estradiol or estradiol derivatives that inhibit colchicine binding to tubulin, by the method given in Example 3.

TABLE 1

| Estrogenic Compound | $IC_{50}$ (μM ± S.D.) |
| --- | --- |
| 2-Methoxyestradiol | 1.9 ± 0.2 |
| Diethylstilbestrol | 2.4 ± 0.4 |
| 2-Bromoestradiol | 4.5 ± 0.6 |
| 2-Methoxyestrone | 8.8 ± 1 |
| 17-Ethynylestradiol | 10.0 ± 2 |
| 2-Fluoroestradiol | 27.0 ± 6 |
| Estradiol | 30.0 ± 6 |
| Estrone | >40 |
| 2-Methoxy-17-ethynylestradiol | >40 |
| Estriol | >40 |
| 2-Methoxyestriol | >40 |
| Estradiol-3-O-methyl ether | >40 |
| 2-Methoxyestradiol-3-O-methyl ether | >40 |
| 4-Methoxyestradiol | >40 |
| 4-Methoxyestradiol-3-O-methyl ether | >40 |
| Plant Products | |
| Colchicine | 0.80 ± 0.07 |
| Podophyllotoxin | 0.46 ± 0.02 |
| Combretastatin A-4 | 0.53 ± 0.05 |
| Dihydrocombretastatin A-4 | 0.63 ± 0.03 |

$IC_{50}$ values are defined as the concentration of an estradiol derivative required to inhibit tubulin polymerization by 50%. $IC_{50}$ values were obtained in at least two independent experiments for non-inhibitory agents ($IC_{50}$ >40 μM) and at least three independent experiments for inhibitory compounds. $IC_{50}$ values were obtained graphically, and average values are presented. S.D., standard deviation.

TABLE 2

| Estrogenic Compound | Percent inhibition ± S.D. |
| --- | --- |
| 2-Methoxyestradiol | 82 ± 2 |
| 2-Methoxyestrone | 57 ± 6 |
| 17-Ethynylestradiol | 50 ± 7 |
| Estradiol | 38 ± 4 |
| Diethylstilbestrol | 30 ± 4 |

Reaction conditions were described in Example 3, with each reaction mixture containing 1.0 μM tubulin, 5% (v/v) dimethyl sulfoxide, 2 μM [³H]colchicine, and 100 μM inhibitor. Incubation was for 10 min at 37° C. Average values obtained in three independent experiments are presented in the table, except for 2-methoxyestrone, which was only examined twice. S.D., standard deviation.

What is claimed is:

1. A method for treating a mammalian disease characterized by undesirable angiogenesis, said method comprising administering to a mammal having said undesirable angiogenesis a compound of the formula below, said compound being administered in an amount sufficient to inhibit angiogenesis:

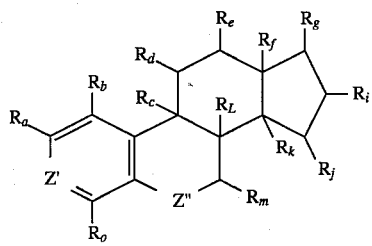

wherein:

I. $R_a$–$R_o$ are defined as follows:

A) each $R_a$, $R_b$, $R_c$, $R_d$, $R_e$, $R_f$, $R_i$, $R_j$, $R_k$, $R_L$, $R_m$, $R_o$, independently is —$R_1$, —$OR_1$, —$OCOR_1$, —$SR_1$, —F, —$NHR_2$, —Br, or —I; and $R_g$ is —$R_1$, —$OR_1$, —$OCOR_1$, —$SR_1$, —F, —$NHR_2$, —Br, —I, or —C≡CH; or B) each $R_a$, $R_b$, $R_c$, $R_f$, $R_k$, $R_L$, $R_o$, independently is —$R_1$, —$OR_1$, —$OCOR_1$, —$SR_1$, —F, —$NHR_2$, —Br, or —I; and each $R_d$, $R_e$, $R_i$, $R_j$, $R_m$, independently is =O, —$R_1$, —$OR_1$, —$OCOR_1$, —$SR_1$, —F, $NHR_2$, —Br or —I; and $R_g$ is =O, —$R_1$, —$OR_1$, —$OCOR_1$, —$SR_1$, —F, —$NHR_2$, —Br, —I, or —C≡CH; and II. Z' is defined as follows:

Z' is X, where X is

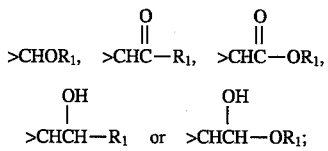

and

III. Z" is defined as follows:

Z" is Y, where Y is

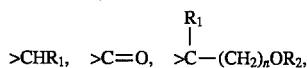

-continued

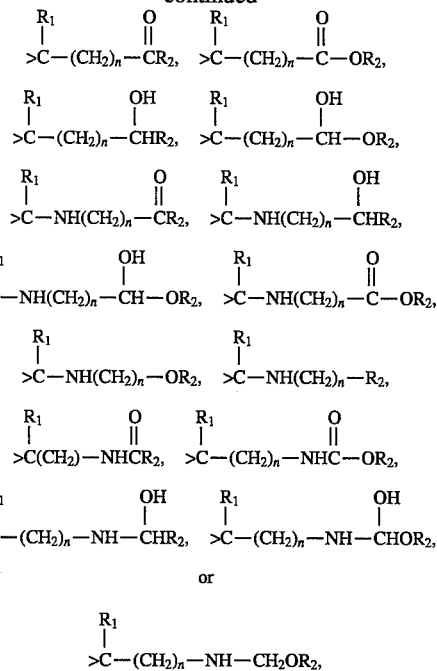

where n is 0–6; and

IV. provided that when each $R_b$, $R_c$, $R_d$, $R_e$, $R_i$, $R_j$, $R_k$, $R_L$, $R_m$ and $R_o$ is H;

$R_f$ is —$CH_3$;

$R_g$ is —OH;

Z' is >COH; and

Z" is >CH2;

then $R_a$ is not —H;

where, in each formula set forth above, each $R_1$ and $R_2$ independently is —H, or an alkyl, alkenyl or alkynl group of up to 6 carbons.

2. The method of claim 1, wherein said compound is 2-methoxyestradiol.

3. The method of claim 1, wherein said compound is 2-fluoroestradiol.

4. The method of claim 1, wherein said compound is 2-bromoestradiol.

5. The method of claim 1, wherein said compound is 2-methoxyestrone.

6. The method of claim 1, wherein said compound is 17-ethynylestradiol.

7. The method of claim 1, wherein at least one of the group consisting of $R_a$–$R_p$ is —OCH3.

* * * * *

UNITED STATES PATENT AND TRADEMARK OFFICE
CERTIFICATE OF CORRECTION

PATENT NO. : 5,504,074
DATED : April 2, 1996
INVENTOR(S) : D'amato et al.

It is certified that error appears in the above-identified patent and that said Letters Patent is hereby corrected as shown below:

Column 3,
Lines 10-15, please delete

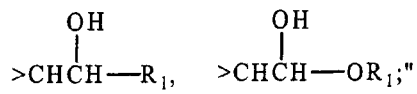

and insert in place thereof

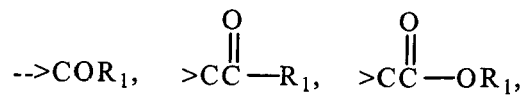

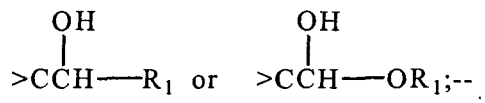

UNITED STATES PATENT AND TRADEMARK OFFICE
CERTIFICATE OF CORRECTION

PATENT NO.   : 5,504,074
DATED        : April 2, 1996
INVENTOR(S)  : D'amato et al.

It is certified that error appears in the above-identified patent and that said Letters Patent is hereby corrected as shown below:

Column 9,
Lines 41-46, please delete

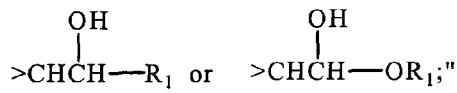

and insert in place thereof

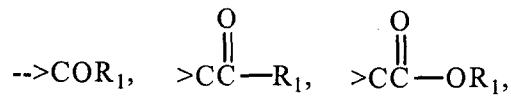

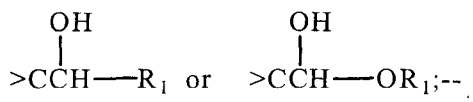

Signed and Sealed this

Seventeenth Day of December, 2002

JAMES E. ROGAN
*Director of the United States Patent and Trademark Office*